United States Patent
Schaefer et al.

(10) Patent No.: US 10,836,718 B2
(45) Date of Patent: Nov. 17, 2020

(54) PROCESS FOR PREPARING ASTACENE

(71) Applicant: BASF SE, Ludwigshafen am Rhein (DE)

(72) Inventors: Bernd Schaefer, Ludwigshafen am Rhein (DE); Wolfgang Siegel, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/462,992

(22) PCT Filed: Nov. 20, 2017

(86) PCT No.: PCT/EP2017/079771
§ 371 (c)(1),
(2) Date: May 22, 2019

(87) PCT Pub. No.: WO2018/095863
PCT Pub. Date: May 31, 2018

(65) Prior Publication Data
US 2019/0292147 A1    Sep. 26, 2019

(30) Foreign Application Priority Data

Nov. 25, 2016  (EP) .................................... 16200804

(51) Int. Cl.
*C07C 403/24* (2006.01)
*C07C 35/00* (2006.01)
*C07C 29/00* (2006.01)

(52) U.S. Cl.
CPC .................................. *C07C 403/24* (2013.01)

(58) Field of Classification Search
CPC ........ C07C 403/24; C07C 35/21; C07C 29/00
See application file for complete search history.

(56) References Cited

U.S. PATENT DOCUMENTS

| 10,017,465 B2 | 7/2018 | Schäfer et al. |
| 2018/0055788 A1 | 3/2018 | Feldthusen Jensen et al. |
| 2018/0110741 A1 | 4/2018 | Feldthusen Jensen et al. |

FOREIGN PATENT DOCUMENTS

| CN | 1817858 A | 8/2006 |
| WO | WO-2016023732 A1 | 2/2016 |
| WO | WO-2016146802 A1 | 9/2016 |
| WO | WO-2016146803 A1 | 9/2016 |
| WO | WO-2018015525 A1 | 1/2018 |

OTHER PUBLICATIONS

International Search Report for PCT/EP2017/079771 dated Jan. 3, 2018.
Written Opinion of the International Searching Authority for PCT/EP2017/079771 dated Jan. 3, 2018.
Kuhn, R., et al., "Über Astaxanthin und Ovoverdin", European Journal of Inorganic Chemistry, Berichte der deutschen chemischen Gesellschaft (A and B Series), vol. 71, Issue 9, Sep. 7, 1938, pp. 1879-1888.

*Primary Examiner* — Sikarl A Witherspoon
(74) *Attorney, Agent, or Firm* — Faegre Drinker Biddle & Reath LLP

(57) ABSTRACT

The invention describes a process for making astacene of formula 1, the exocyclic double bonds thereof having either an E configuration or an E- and/or Z-configuration, wherein astaxanthin of the general formula 2 having asymmetric centers 3 and 3', each of which respectively having an (S)- or (R)-conformation and the exocyclic double bonds of said astaxanthin 2 having either an E- or E- and/or Z configuration, is oxidized in the presence of at least one tertiary alcoholate.

21 Claims, No Drawings

PROCESS FOR PREPARING ASTACENE

CROSS-REFERENCE TO RELATED APPLICATIONS

This application is a national stage application (under 35 U.S.C. § 371) of PCT/EP2017/079771, filed Nov. 20, 2017, which claims benefit of European Application No. 16200804.9, filed Nov. 25, 2016, both of which are incorporated herein by reference in their entirety.

This invention deals with a straight forward process to obtain astacene. A further embodiment of the invention devises a process for obtaining enantiomerically pure astaxanthin or astaxanthin with a high enantiomeric excess. Yet another embodiment of the invention comprises a preparation comprising enantiomerically pure astaxanthin or astaxanthin exhibiting a high enantiomeric excess.

In 1938 it was postulated, that astacene is an oxidative artefact of astaxanthin and said astaxanthin can be converted into astacene in an alkaline environment supplemented with oxygen. This was deduced from the consumption of two moles of oxygen per mol of astaxanthin, yielding hydrogen peroxide and presumably astacene (cf. R. Kuhn, N. A. Sörensen Chem. Ber. 1938 71, 1879-1888, p. 1880, para 1). However, if at all, the consumption of oxygen is only an indirect pointer of astacene formation. Even if astacene really forms, which is not clear, said reaction described by Kuhn et al. requires at least eight hours. Furthermore also hydrogen peroxide formation takes place, which certainly has an impact on the stability of astacene, an entity exhibiting 4 cyclic double bonds and 9 exocyclic double bonds.

In CN 1817858 A filed on Mar. 16, 2006 astacene is synthesized in a two-step reaction starting from astaxanthin. In fact, astaxanthin is suspended in an alcohol and contacted with an alkaline substance. Said alkaline substance is selected from the group consisting of sodium methoxide, sodium ethoxide, sodium hydroxide, potassium hydroxide, with sodium methoxide and potassium hydroxide being preferred. The reaction is conducted under an oxygen atmosphere at a temperature of 30° C. to 80° C. while agitating. Between 0.6 and 18 l of oxygen are required per hour. The reaction time according to the examples ranges from 7 to 28 hours. At the end of the reaction one obtains a solid crude product, which in fact is a mixture of unreacted astaxanthin and astacene both in an ionized form. Said crude solid is contacted with dichloromethane and filtered. Unreacted astaxanthin remains in the filtrate whereas ionized astacene does not dissolve. In a second step said ionized astacene is dissolved in water to give an alkaline reaction solution, which is neutralized to a pH of 4 to 6 by means of an acid. This neutralization step converts the ionized form of astacene into neutralized astacene.

This reaction of the prior art suffers from several drawbacks: It must be conducted under oxygen, which is to say one works with a heated organic solvent in an atmosphere of oxygen, thus with an explosive mixture. Such explosive mixtures can only be handled safely in pressure resistant means like autoclaves, making the reaction very expensive on an industrial scale. In addition the reaction time of at least 7 hours is quite long. Another drawback is the tedious treatment of the solid crude product. Furthermore the yields based on the starting material are not very high and range from about 38 to about 68 w %.

It thus was an object of the invention to overcome the drawbacks of the prior art and to devise an improved and safe process for producing astacene from astaxanthin which is straightforward and does not generate a huge amount of by-products. Especially over-oxidized products and multiple reaction steps shall be avoided or at least reduced. The process shall be fast, cost-effective and energy saving. Costly protective measures to avoid explosion shall be avoided. It shall furnish high, almost total conversion as well as high yields of pure reaction product astacene. Large amounts of metal ions in the final product shall be avoided. At the same time one is to avoid cumbersome treatment or processing of intermediates or crude products. The process furthermore needs to be realized on an industrial scale.

A further object of the invention consists in providing a cheap, short and straightforward process for making entantiomerically pure astaxanthin or enantiomerically highly enriched astaxanthin from a racemic astaxanthin mixture. Said process likewise shall not generate a huge amount of by-products. Multiple reaction steps shall be avoided or at least reduced. The process shall be fast, cost-effective and energy saving. It shall furnish high conversion as well as high yields of pure or enantiomerically highly enriched astaxanthin. Large amounts of metal ions in the final product shall be avoided. At the same time one is to avoid cumbersome treatment or processing of intermediates or crude products. Likewise this embodiment of the inventive process needs to be realized on an industrial scale.

Still another object of the invention is to provide a nontherapeutic preparation comprising enantiomerically pure astaxanthin or an astaxanthin highly enriched in enantiomerically pure astaxanthin. It is still a further object to make a preparation for a pharmaceutical or medical use comprising enantiomerically pure astaxanthin, or an astaxanthin highly enriched in enantiomerically pure astaxanthin.

The previously set up requirements are met by a process for making astacene of formula 1, the exocyclic double bonds thereof having either an E configuration or an E- and/or Z-configuration

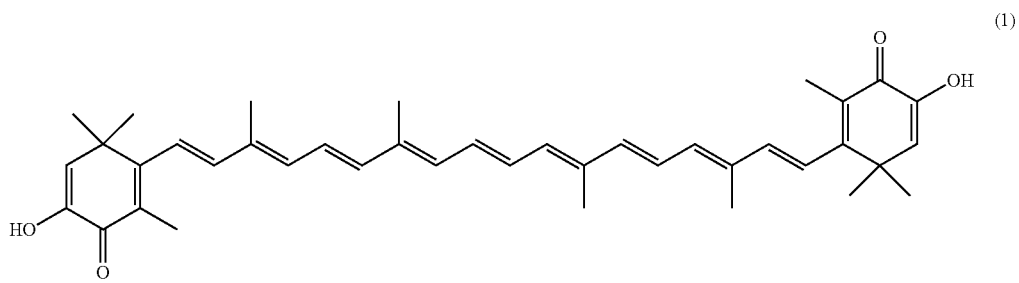 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

(1)

wherein astaxanthin of the general formula 2

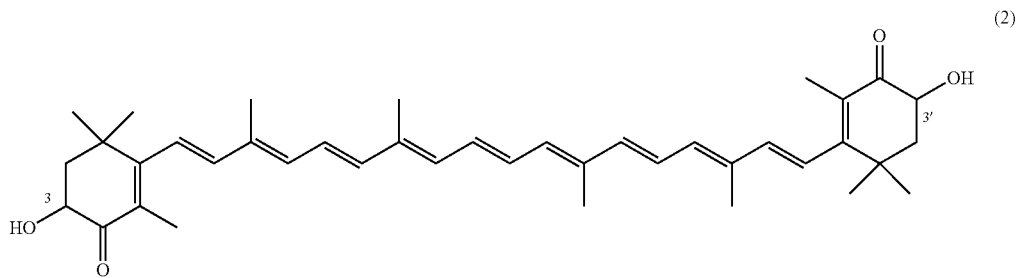

(2)

having asymmetric centers 3 and 3', each of which respectively having an (S)- or (R)-conformation and the exocyclic double bonds of said astaxanthin 2 having either an E- or E- and/or Z configuration, is oxidized in the presence of at least one tertiary alcoholate.

This feature leads to hitherto unknown high yields and purities of astacene of formula 1 as shown in the examples below. Working under an oxygen atmosphere and thus necessary explosion protection means are no longer required. The reaction time is about 2 h, thus pretty fast and nevertheless the reaction shows much better conversion as well as yields than the prior art. Considerable amounts of unreacted astaxanthin of the general formula 2 do not remain. Said amounts are a main drawback of the prior art and were expected for this reaction as well, due to the short reaction time. Elaborated filtration steps are not necessary as in the prior art and a huge amount of by-products especially over-oxidized products cannot be observed.

The possibility of obtaining astacene in high yield from astaxanthin by the claimed process is surprising, since subjecting astaxanthin to conditions of an Oppenauer oxidation did not give any astacene. The Oppenauer catalyst used was $Al(OR)_3$ with R being phenyl.

A tertiary alcoholate is understood to be any compound, which can be obtained from a tertiary alcohol contacted with a metal or metal compound, thus forming the deprotonated tertiary alcohol or alcohol anion with the metal ion as the counter ion. This process generally liberates hydrogen or a hydrogen halide. The term "tertiary" according to this disclosure denotes any entity having a central carbon, which is surrounded by three alkyl groups, with "alkyl" meaning any entity consisting of carbon and hydrogen atoms.

Yields and conversion rates or potencies in this disclosure are given in percent by weight based on the starting material astaxanthin. This appears to be reasonable, since astaxanthin has a molecular weight of 596.841 g/mol and astacene of 592.81, viz. percentage yields based on moles would only differ in the second position after decimal point compared to percentage yields based on weight. This can be neglected since only values before the decimal point are considered and compared with the prior art.

The term "molar equivalent" denotes the molar multiple of the indicated compound used with respect to molar amount of astaxanthin 2 used.

"Metal salt" within the disclosure of this invention is understood to be any salt which can form by assembly of a metal cation and an anion. However, expressively excluded from this term "metal salt" are hydroxyl compounds of alkali and earth alkali metals. Likewise alcoholates of alkali and earth alkali metals, viz deprotonated alcohols having an alkali or earth alkali metal as counter ion, do not make part of the term "metal salt".

"Transition metal salt" for the purpose of this disclosure has the same meaning as "metal salt", however, only including the metals belonging to groups 3 to 12 of the periodic table.

The term "salts of transition metals" is a subgroup of a "transition metal salt" including at least one anion which is selected from the group consisting of halide ions, nitrate, sulfate, phosphate, tosylate, C1-C6 carboxylate meaning a carboxylate having from 1 to 6 carbon atoms, C1-C4 sulfonate being a sulfonate having from 1 to 4 carbon atoms, trifluoromethanesulfonate.

A "divalent salt of a transition metal" is a salt of a transition metal with the transition metal having the oxidation state II.

A "trivalent salt of a transition metal" is a salt of a transition metal with the transition metal having the oxidation state III.

"Oxides of transition metals" is another subgroup of a transition metal salt only including oxides of transition metals.

The term "enantiomeric excess" or "ee" within this disclosure is understood to be the percent enantiomer excess of a chemical compound. For a mixture of (+) and (−) enantiomers, the amount of each enantiomer being given as the mole or weight fractions $F_{(+)}$ and $F_{(−)}$ (where $F_{(+)}+F_{(−)}=1$), the enantiomer excess is defined as $|F_{(+)}-F_{(−)}|$ and the percent enantiomer excess corresponding to enantiomeric excess as used in this disclosure is defined as $100*((|F_{(+)}-F_{(−)}|)/(F_{(+)}+F_{(−)}))$. The enantiomeric excess is expressed in % like for instance "ee 94%") For further details, refer to IUPAC, *Compendium of Chemical Terminology*, 2nd ed. (the "Gold Book") (1997). Online corrected version: (1996) "Enantiomer excess".

The wording "diastereomeric excess" or "de" as understood within this text means the percent diastereomer excess of a chemical compound. For a mixture of diastereomer 1 and diastereomer 2, the amount of each dianstereomer being given as the mole or weight fractions $D_{(1)}$ and $D_{(2)}$ (where $D_{(1)}+D_{(2)}=1$), the diastereomer excess is defined as $|D_{(1)}-D_{(2)}|$ and the percent diastereomer excess corresponding to diastereomeric excess as used in this disclosure is defined as $100*((|D_{(1)}-D_{(2)}|)/(D_{(1)}+D_{(2)}))$. The diastereomeric excess is expressed in % like for instance "de 92%") For further details, refer to IUPAC, *Compendium of Chemical Terminology*, 2nd ed. (the "Gold Book") (1997). Online corrected version: (1996) "Diastereomer excess".

"Astaxanthin highly enriched in astaxanthin of formula 3 or of formula 5" means an astaxanthin sample comprising at least 95 w % of compound of formula 3 and at most 5 w % of compound of formula 5 or an astaxanthin sample comprising at least 95 w % of compound of formula 5 and at most 5 w % of compound of formula 3.

"Enantioselective transfer hydrogenation" as employed in this disclosure is understood to be an enantioselective addition of hydrogen to a molecule from a source other than gaseous $H_2$.

"Without any workup" as disclosed herein means realizing a further process or reaction step without entirely removing one of the reactants or solvents of the previous process or reaction step. Removing only a partial amount of a reactant or a solvent is not considered to fall under the term "without any work-up".

"One-pot" is to say that a chemical reaction realized or a sequence of chemical reactions realized take place in one and the same recipient and only the final product of the chemical reaction or of the sequence of chemical reactions is removed from said recipient as is or, for instance for further purification.

A further developed embodiment of the invention comprises the process for making astacene of formula 1, the exocyclic double bonds thereof having either an E configuration or an E- and/or Z-configuration having asymmetric centers 3 and 3', each of which respectively having an (S)- or (R)-conformation and the exocyclic double bonds of said astaxanthin 2 having either an E- or E- and/or Z configuration, is oxidized in the presence of at least one tertiary alcoholate, and said astaxanthin 2 is added into the reaction means in multiple portions.

Multiple portions means from 3 to 20 portions, preferably from 4 to 15 portions and highly preferred from 6 to 10 portions.

This measure provides for working with much higher concentrated reaction mixtures, which is to say, per time more astaxanthin of the general formula 2 can be converted into astacene of formula 1.

Besides this embodiment or in addition to this embodiment, the inventive process is suited to be run batchwise, semibachtwise (meaning that only one or several selected reagents are added to the reaction mixture) or continuously in reactor cascades or in a tubular reactor.

A further considerable feature of the inventive process is the amount of the at least one tertiary alcoholate used. As can be gleaned from the examples, high yields of astacene 2 are obtained, when the total amount of tertiary alcoholate used ranges from 2 to 25 molar equivalents based on the amount of astaxanthin 2 used, preferably from 3 to 20 molar equivalents and mostly preferred from 4 to 20 molar equivalents. For some embodiments of the inventive process, total amounts of tertiary alcoholate ranging from 15 to 25 molar equivalents, preferably from 18 to 20 molar equivalents based on the amount of astaxanthin 2 used were shown to give the highest yields of astacene 1. These embodiments inter alia include such, which are not realized in a "one-pot" reaction

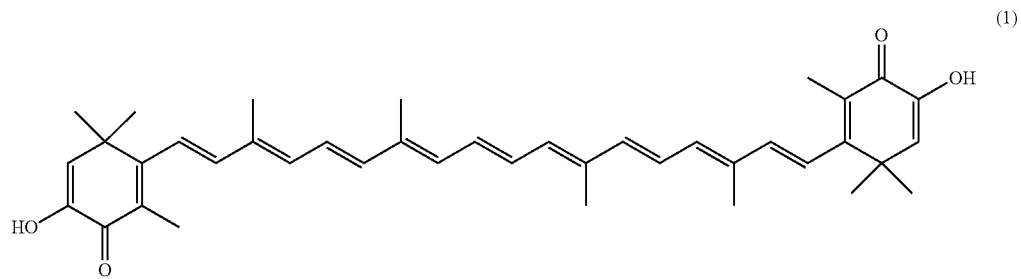 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

(1)

wherein astaxanthin of the general formula 2

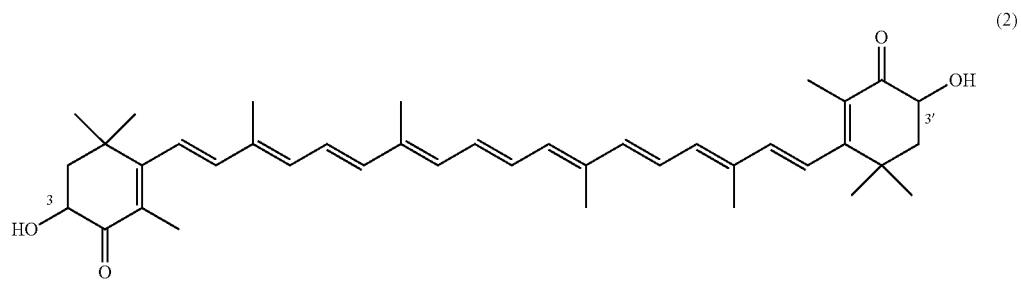

(2)

Thus another embodiment of the inventive process for making astacene of formula 1, the exocyclic double bonds thereof having either an E configuration or an E- and/or Z-configuration

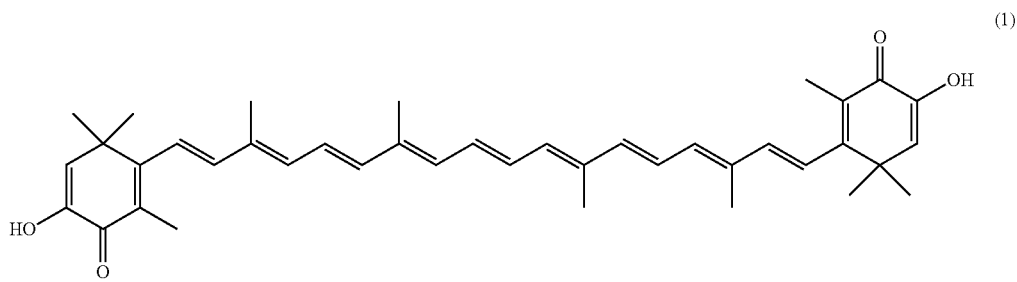 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

discloses that astaxanthin of the general formula 2

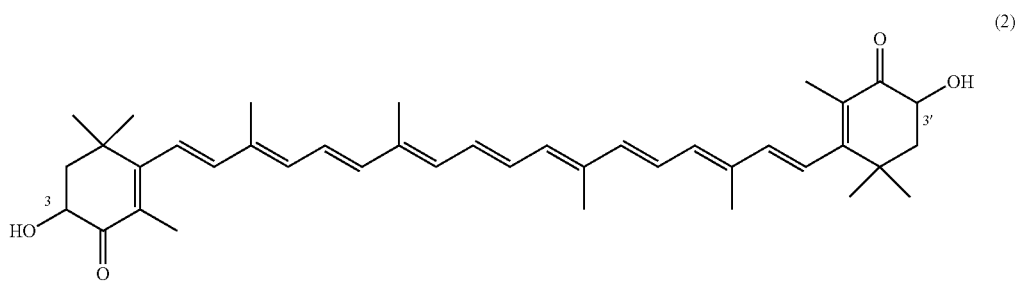

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate, the amount of all tertiary alcoholate used ranging from 2 to 25 molar equivalents based on the amount of astaxanthin 2 used, preferably from 3 to 20 molar equivalents and mostly preferred from 4 to 20 molar equivalents.

The experiments showed the cation of the tertiary alcoholate to have an influence both on reaction time and yield. "$K^+$" and "$Na^+$" proved to be a better candidate compared to other cations. The invention thus provides in an additional embodiment, that the at least one tertiary alcoholate bears at least one counter ion selected from the group consisting of $K^+$, $Na^+$ and preferably being K.

The type of stirrer used was also determined to influence the yield of the inventive process. Higher yields were realized by means of a lab scale impeller compared to a disk stirrer. The invention thus also requires protection for an embodiment disclosing a process for making astacene of formula 1, the exocyclic double bonds thereof having either an E configuration or an E- and/or Z-configuration

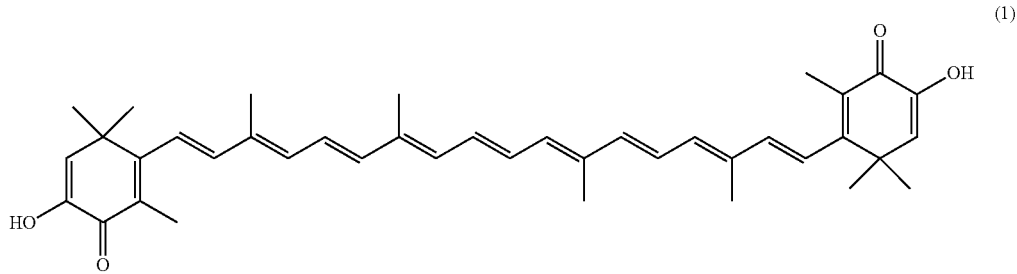 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

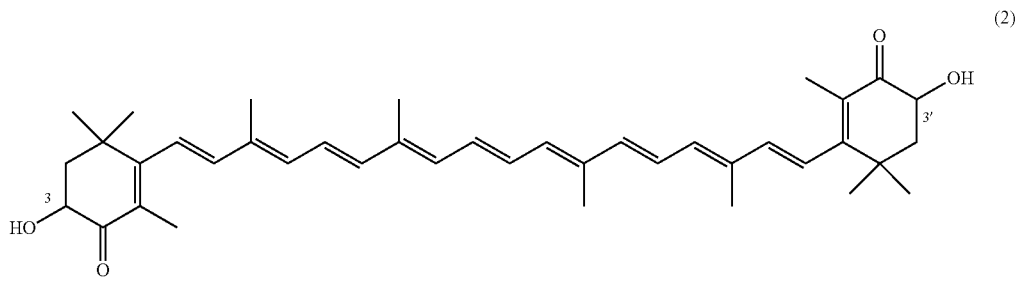

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate, said oxidation being realized with an impeller as mixing means.

A solvent saving embodiment of the invention is a process for making astacene of formula 1, the exocyclic double bonds thereof having either an E configuration or an E- and/or Z-configuration

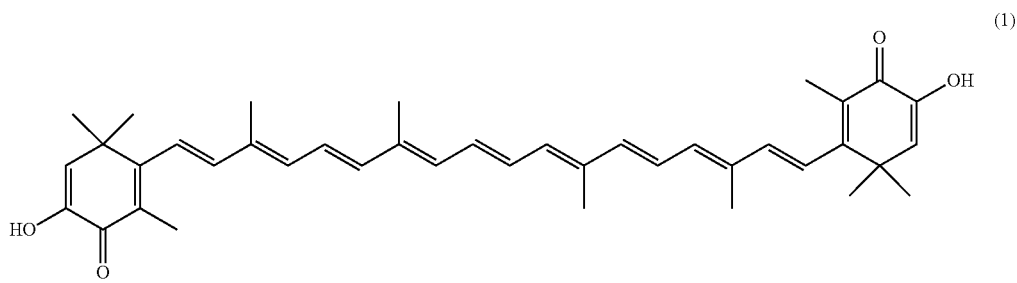 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

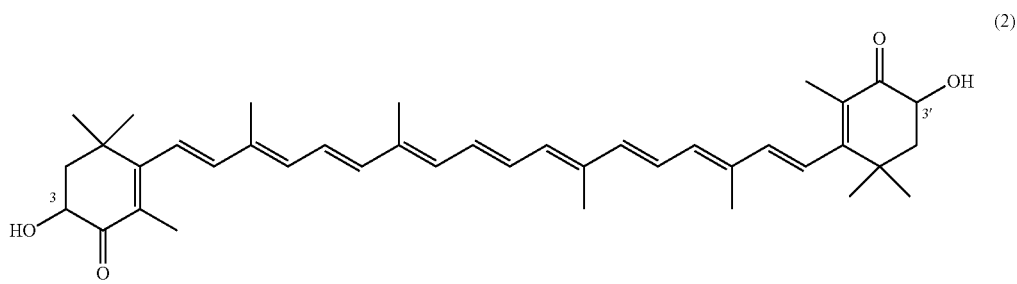

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate, said at least one tertiary alcoholate being the process solvent.

However, upon using small amounts of tertiary alcoholate, the inventive process is realized in a solvent. Such process for making astacene of formula 1, the exocyclic double bonds thereof having either an E configuration or an E- and/or Z-configuration

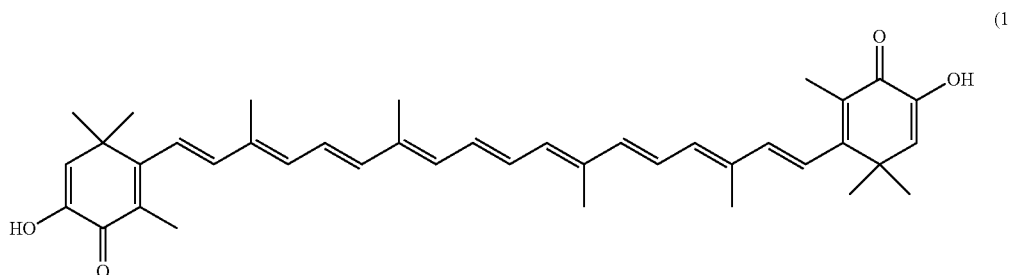

describes astaxanthin of the general formula 2

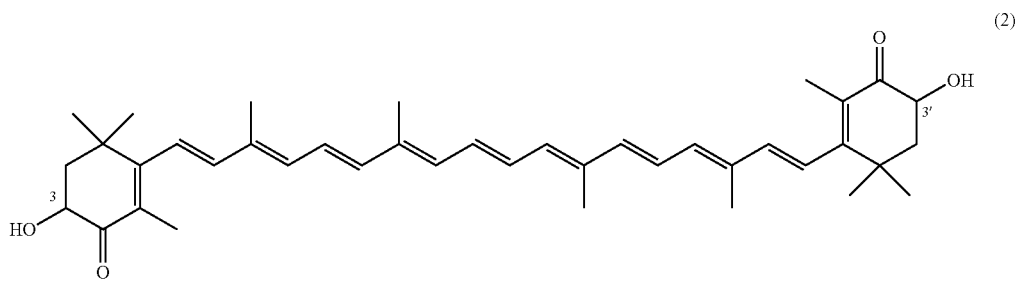

having asymmetric centers 3 and 3', each of which respectively having an (S)- or (R)-conformation and the exocyclic double bonds of said astaxanthin 2 having either an E- or E- and/or Z configuration,
to be oxidized
  in a solvent or solvent mixture which is selected from the group comprising, preferably consisting of, chlorinated C6-C8-aromates, C4-C8-ethers, C1-C6-alcohols, halogenated C1-C4-hydrocarbons, C2-C4-nitriles, C2-C7-esters, and
  in the presence of at least one tertiary alcoholate.

Chlorinated C6-C8-aromates are understood to comprise at least one of the following compounds chlorobenzene, 2-chlorotoluene, and its isomers, chloroxylene and its isomers. A highly preferred C6-C8-aromate is chlorobenzene.

The group of C4-C8 ethers comprises at least one of the following compounds ethyleneglycold imethylether, diethyleneglycoldimethylether, tetrahydrofuran, dioxane, 2-methyl-tetrahyd rofuran, methyl-tert.-butylether, dipropylether, diisopropylether, diethylether, methylisopropylether, di-n-butylether, dicyclopentylether, cyclopentylmethylether. Highly preferred is di-n-butyl ether.

The group of C1-06 alcohols consists of at least one of the alcohols methanol, ethanol, 2-methoxyethanol, ethylenglycol, n-propanol, isopropanol, 2-methoxy-1-propanol, propylenglycol, 1,2-propandiol, 1,3-popandiol, n-butanol, sec.-butanol, isobutanol, tert.-butanol, 1,2-butandiol, 1,3-butandiol, 1,4-butandiol, 2,3-butandiol, 2-methyl-2,3-butandiol, 1,2,3-butantriol, 1,2,4-butantriol, diethylenglykol, n-pentanol, 2-pentanol, isopentylalcohol, isoamylalcohol or 3-pentanol, 2-methyl-1-butanol, neopentylalcohol, tert.-pentylalcohl, 1,5-pentandiol, 1,4-pentandiol, 1,3-pentandiol, 1,2-pentandiol, 2,4-pentandiol cyclopentanol, cyclohexanol, n-hexanol, 1,3-dimethylbutanol or amylmethylalcohol, diacetonalcohol, methylisobutylcarbinol, tert.-hexylalcohol, 1,6-hexandiol, 1,5 hexandiol, 1,4-hexandiol, 1,3-hexandiol, 2-methyl-2,4-pentandiol, pinakol or 2,3-dimethyl-2,3-butandiol, glycerin, 1,2,5-hexantriol, 1,2,6-hexantriol, trimethylolpropane. From these alcohofs t-butanol is highly preferred, since it gives good yields compared to other solvents as can be seen in the examples below.

Halogenated C1-C4 hydrocarbons are meant to comprise dichloromethane, trichloromethane, tetrachloromethane, dichloroethane, tetrachloroethylene, 1,1,2,2-tetrachloroethane of which dichloromethane, 1,2-dichloroethane, trichloromethane and 1,1,2,2-tetrachloroethane are highly preferred.

C2-C4-nitriles comprise a group of compounds consisting of acetonitrile, propionitrile, butyronitrile, isobutyronitrile. A preferred candidate is acetonitrile.

Esters comprising between 2 and 7 carbon atoms (C2-C7-esters) likewise serve as solvent and comprise at least one entity selected from the group comprising, preferably consisting of methyl formate, ethyl formate, n-propyl formate, iso-proyl formate, n-butyl formate, methyl acetate, ethyl acetate, n-propyl acetate, iso-propyl acetate, n-butyl acetate, methyl propionate, ethyl propionate, n-propyl propionate, iso-propyl propionate, n-butyl propionate. A preferred candidate is ethyl acetate.

Among these solvents, t-butanol showed the most appropriate capacity for dissolving the compounds of the inventive process.

Tertiary alcoholates are mandatory for the inventive process since secondary or primary alcoholates like for instance sodium methanolate and sodium ethanolate could not afford the high yield and the reduced reaction time. Among the tertiary alcoholates as defined supra, those of the type C4-C6 alcoholate are highly preferred for cost reasons. The tertiary C4-C6 alcoholates comprise between 4 and 6 carbon atoms. They are selected from the group comprising, preferably consisting of, tert.-butanolate, 2-methylbutan-2-olate, 1,1-dimethylpropan-1-olate, 1,1-dimethylbutan-1-olate.

Taking into account this observation another embodiment of the invention discloses a process for making astacene of formula 1, the exocyclic double bonds thereof having either an E configuration or an E- and/or Z-configuration

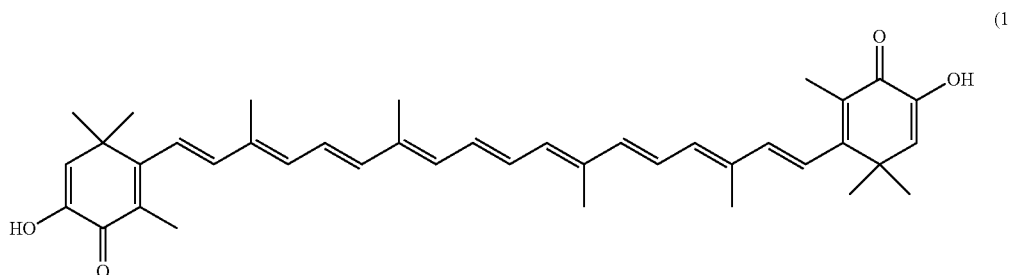

wherein astaxanthin of the general formula 2

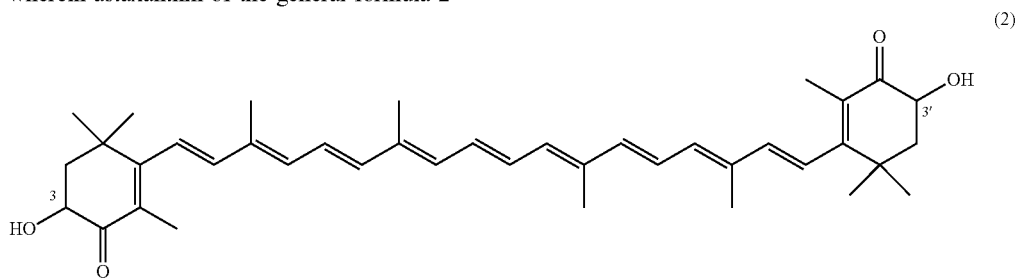

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary C4-C6-alcoholate, the amount of all tertiary alcoholate used ranging from 2 to 25 molar equivalents based on the amount of astaxanthin 2 used, preferably from 3 to 20 molar equivalents and mostly preferred from 4 to 20 molar equivalents.

From the examples one observes that the yield of astacene 1 and conversion of astaxanthin 2 are increased if astaxanthin of the general formula 2 is oxidized in the presence of at least one metal salt. The metal salt is a salt as defined supra.

This in particular holds, if the metal salt is a transition metal salt selected from the group of salts of transition metals and/or from the group of oxides of transition metals, preferably from divalent and/or trivalent salts of transition metals, further preferred from divalent and/or trivalent salts of transition metals of the group consisting of Mn, Co, Fe, Cu Ru, and highly preferred from divalent and/or trivalent salts of transition metals of the group consisting of Mn(II), Co(II), Fe(II), Cu(II) and Ru(III).

A transition metal salt is understood to be at least one salt selected from the group of metals consisting of Cu, Co. Ru, Mn, Cr. Ti, V, Fe, Ni, Pd, Pt, Ag, Zr, Mo, Rh, W, Re, Os, Ir, Au and Hg. Good yields of astacene 1 and high conversion of astaxanthin 2 during a short reaction time were shown to be obtained with at least one transition metal salt selected from the group of metals consisting of Mn, Co, Fe, Cu, Ru.

A preferred salt of a transition metal is a salt including at least one anion, preferably only including at least one anion, which is selected from the group consisting of halide ions, nitrate, sulfate, phosphate, tosylate, C1-C6 carboxylate, C1-C4 sulfonate, trifluoromethanesulfonate, as defined supra, and having as cation at least one of the metals selected from the group consisting of Cu, Co. Ru, Mn, Cr. Ti, V, Fe, Ni, Pd, Pt, Ag, Zr, Mo, Rh, W, Re, Os, Ir, Au and Hg. More preferred said salt of a transition metal is a salt including at least one anion, preferably only including at least one anion, which is selected from the group consisting of halide ions, nitrate, sulfate, phosphate, tosylate, C1-C6 carboxylate, C1-C4 sulfonate, trifluoromethanesulfonate, as defined supra, and having as cation at least one of the metals selected from the group of metals consisting of Mn, Co, Fe, Cu, Ru. Highly preferred said salt of a transition metal is a salt including at least one anion, preferably only including at least one anion, which is selected from the group consisting of halide ions, nitrate, sulfate, phosphate, tosylate, C1-C6 carboxylate, C1-C4 sulfonate, trifluoromethanesulfonate, as defined supra, and having as cation at least one of the metals selected from the group of metals consisting of Mn(II), Co(II), Fe(II), Cu(II), Ru(III).

A further preferred salt of a transition metal is a divalent or trivalent salt of a transition metal, in particular a divalent or trivalent salt of a transition metal as disclosed in the previous paragraph.

An oxide of a transition metal is at least one compound selected from the group comprising preferably consisting of $MnO_2$, $Co_2O_3$, FeO, $Fe_2O_3$, CuO, $Cu_2O$, $Ru_2O_3$, $MnO_2$, $Fe_2O_3$, $Ru_2O_3$.

Among other anions experiments showed such metal salt to be highly compatible with the reaction mixture, which comprises at least one anion, preferably only at least one anion, said at least one anion being selected from the group consisting of halide ions, C1-C6-carboxylate, nitrate, sulfate, phosphate, C1-C4-sulfonate, trifluoromethanesulfonate, tosylate.

Only little amounts of metal salt were observed to be required for influencing the conversion of astaxanthin of the general formula 2 into astacene 1. This is advantageous, since the product astacene 1 is required to contain an amount of metal ions as low as possible, which otherwise have to be removed laboriously in a later step.

Therefore protection is also sought for a process for making astacene of formula 1, the exocyclic double bonds thereof having either an E configuration or an E- and/or Z-configuration

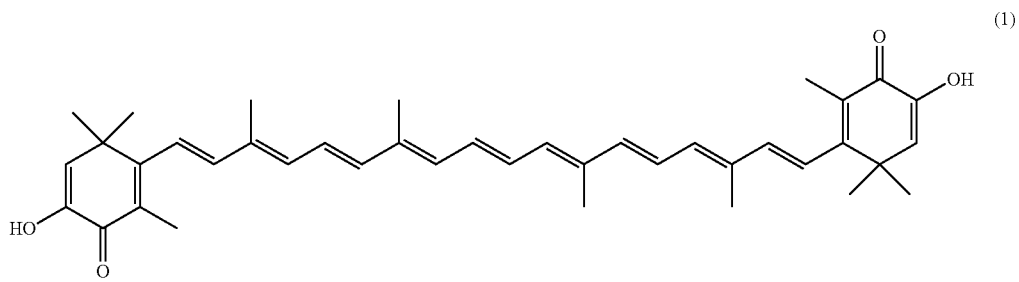 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

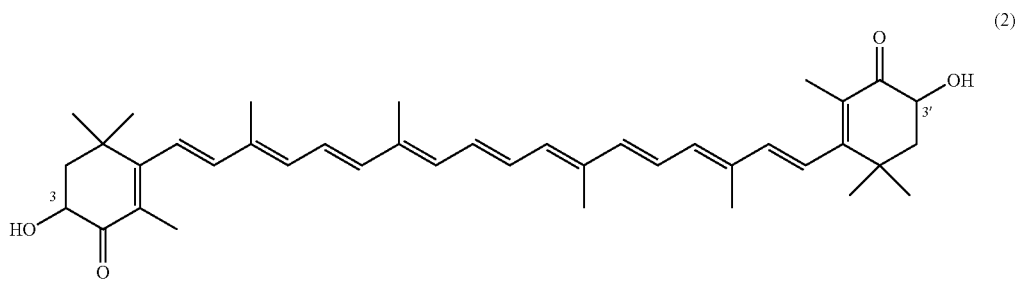

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate and of at least one metal salt, the amount of metal salt used in total ranging from 0 to 4 mol % based on the amount of astaxanthin of the general formula 2 used, preferably from 0.05 to 2 mol % and most preferably from 0.1 to 1 mol %.

The metal salt used in the previous embodiment is preferably a transition metal salt selected from the group of salts of transition metals and/or from the group of oxides of transition metals, more preferably from divalent and/or trivalent salts of transition metals, further preferred from divalent and/or trivalent salts of transition metals of the group consisting of Mn, Co, Fe, Cu, Ru, and highly preferred from divalent and/or trivalent salts of transition metals of the group consisting of Mn(II), Co(II), Fe(II), Cu(II) and Ru(III).

In a further developed embodiment of the inventive process a nitrogen compound was found to be of importance, since it complexes the cations of the tertiary alcoholate used. Thus protection is also sought for oxidizing astaxanthin of the general formula 2 in the presence of at least one nitrogen compound, said at least one nitrogen compound being selected from the group comprising, preferably consisting of, tertiary amines, pyridine, diamines and dipyridine, of which N,N,N,N-tetramethylethylendiamine (TMEDA) is highly preferred. This may be attributed to the existence of the cation chelating like character of N,N,N,N-tetramethylethylendiamine (TMEDA) making the tertiary alcoholate anion even more unshielded.

It was proven to be sufficient to use the nitrogen compound in a molar amount which is far below the amount of astaxanthin used. Thus a further elaborated embodiment of the invention comprises a process for making astacene of formula 1, the exocyclic double bonds thereof having either an E configuration or an E- and/or Z-configuration

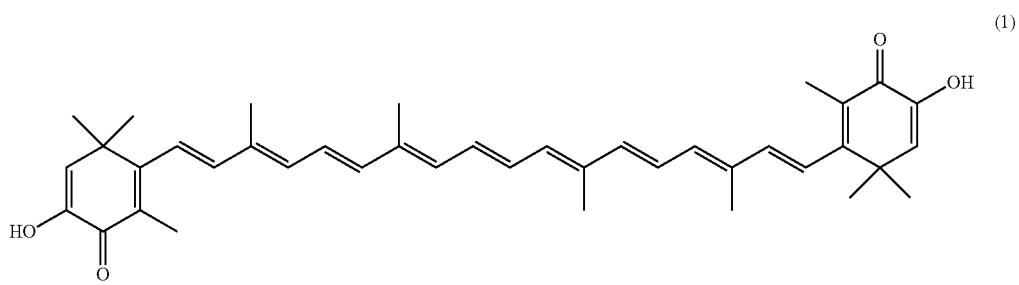 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

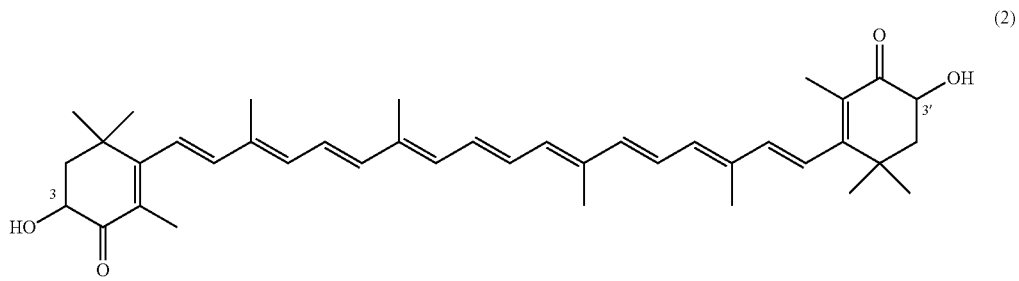

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate and
at least one nitrogen compound, said at least one nitrogen compound being selected from the group comprising, preferably consisting of, tertiary amines, pyridine, diamines and dipyridine and the nitrogen compound being used in an amount ranging from 0 to 0.1 molar equivalents of astaxanthin 2 used, preferably from 0 to 0.06 molar equivalents and mostly preferred from 0 to 0.02 molar equivalents.

Nitrogen compounds were found to have a beneficial effect on the reaction yield after a short reaction time. However, they can also be avoided provided the amount of tertiary alcoholate used is reduced. To cover this result a further embodiment of the invention discloses a process for making astacene of formula 1, the exocyclic double bonds thereof having either an E configuration or an E- and/or Z-configuration having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate, the amount of all tertiary alcoholate used ranging from 2 to 10 molar equivalents based on the amount of astaxanthin 2 used, preferably from 3 to 8 molar equivalents and mostly preferred from 4 to 6 molar equivalents.

The prior art oxidation of astaxanthin to form astacene takes as already said between 7 and 28 h and thus is very time-consuming. The newly devised process provides higher yields in less time. Therefore a further embodiment of the invention is a process for making astacene of formula 1, wherein astaxanthin of the general formula 2 is oxidized in the presence of at least one tertiary alcoholate in a time ranging from 0.25 h to 6 h, preferably ranging from 0.5 to 5 h, more preferably from 1 to 4 h and mostly preferred from 2 to 3 h. Said embodiment is cost-effective and provides more astacene 1 per time.

Reaction temperatures in the prior art range from 55 to 80° C. Only one example can work with a temperature of

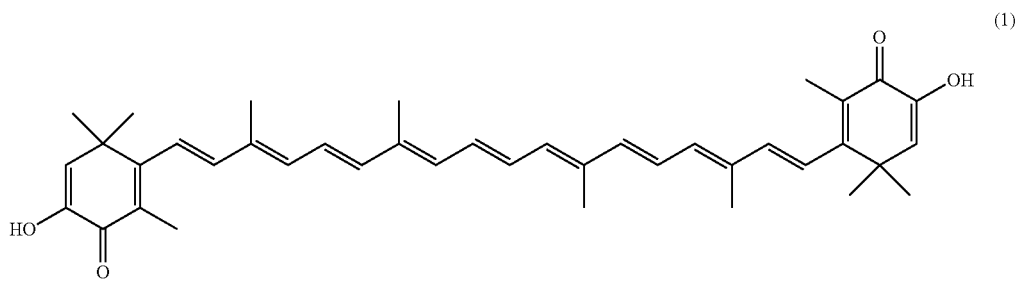 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

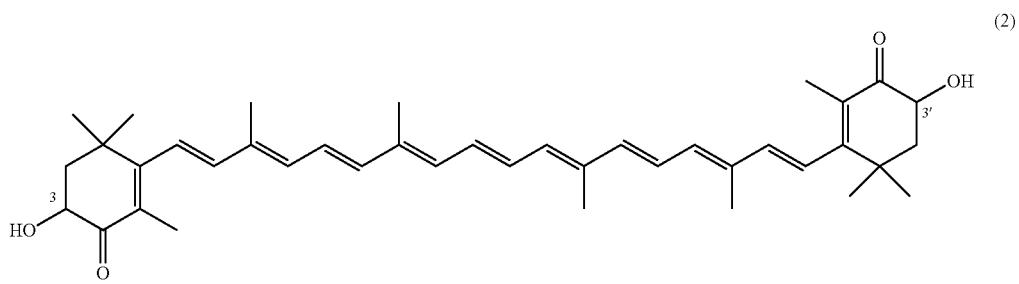

30° C., however, at the expense of a long reaction time of 25 h. As can be seen from the examples below, the newly devised process is conducted at moderate temperatures and is thus favorable over the prior art. This is reflected by a further embodiment of the invention disclosing a process for making astacene of formula 1, the exocyclic double bonds thereof having either an E configuration or an E- and/or Z-configuration

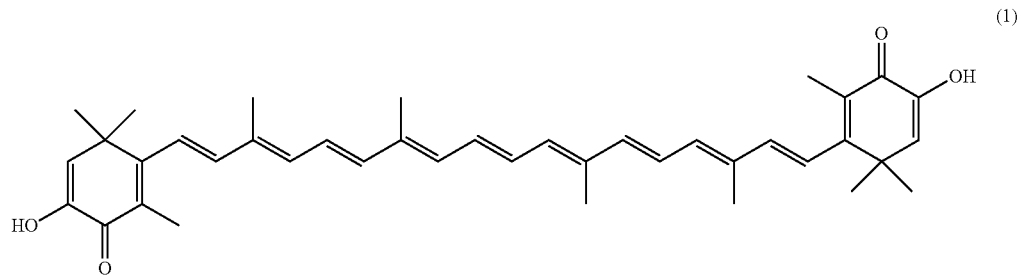 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

wherein astaxanthin of the general formula 2

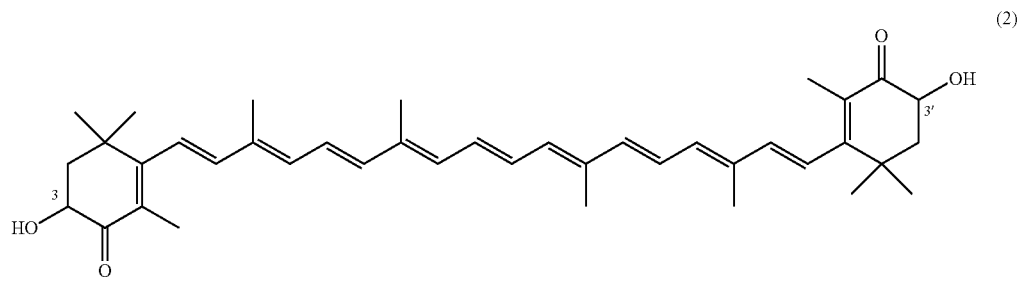

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate at a temperature ranging from 0° C. to 40° C., preferably from to 21° C. to 40° C.

The advantage over the prior art is even more apparent in an embodiment of the inventive process for making astacene of formula 1, the exocyclic double bonds thereof having either an E configuration or an E- and/or Z-configuration

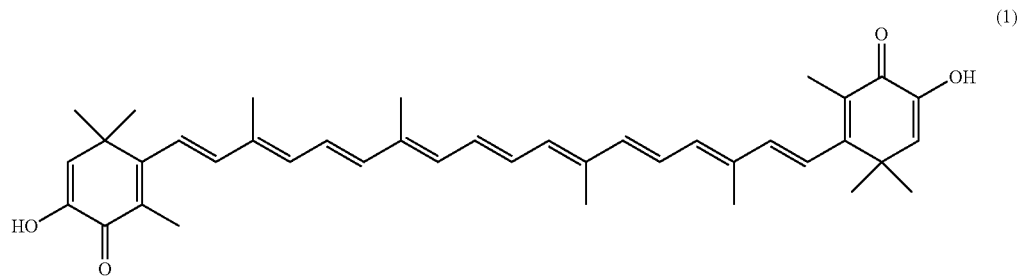 [SMILES: CC1=C(/C=C/C(C)=C/C=C/C(C)=C/C=C/C=C(C)/C=C/C=C(C)/C=C/C2=C(C)C(=O)C(O)=CC2(C)C)C(C)(C)C=C(O)C1=O]

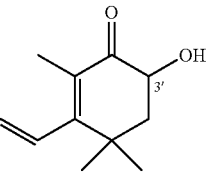
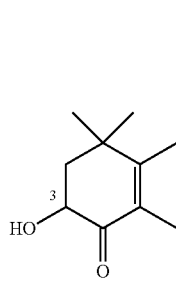

(2)

having asymmetric centers 3 and 3', each of which respectively having an (S)- or (R)-conformation and the exocyclic double bonds of said astaxanthin 2 having either an E- or E- and/or Z configuration,
is oxidized in the presence of at least one tertiary alcoholate at a temperature ranging from 0° C. to 40° C., preferably from to 21° C. to 40° C. and in a time ranging from 0.25 h to 6 h, preferably ranging from 0.5 to 5 h, more preferably from 1 to 4 h and mostly preferred from 2 to 3 h.

The already known reactions for converting astaxanthin into astacene suffer from the huge drawback of requiring an oxygen atmosphere as already mentioned supra. The inventive process avoids this by oxidizing astaxanthin of the general formula 2 in an atmosphere of an inert gas, or in an atmosphere of a mixture of air and an inert gas, or in an air atmosphere, said respective atmospheres comprise from 0 to 50 vol % of oxygen, preferably from 5 to 30 vol %, more preferably from 6 to 20 vol % and most preferably from 7 to 15 vol %. Due to this feature, the inventive process is much less expensive, in particular on a large scale, since explosion protection means can be avoided.

The term "inert gas" within this disclosure is meant to be at least one gas selected from the group consisting of nitrogen, argon, carbon dioxide.

The gas or gases of the respective atmosphere required are supplemented to the reaction vessel either separately or as a mixture. They are either introduced into the reaction mixture or thy pass over the reaction mixture. Gassing means for chemical reactions like gassing stirrers or reaction mixing pumps and reaction mixing nozzles are used for this.

The process of the invention is suited to be realized at low pressure, ambient pressure or under pressure load, with pressures ranging from ambient pressure up to 10 bars being highly preferred.

The inventive process experiences a considerable continuation with the following embodiment. It is a process for preparing from a mixture of various astaxanthin isomers of general formula 2 an enantiomerically pure astaxanthin of formula 3 or of formula 5, or an astaxanthin highly enriched in astaxanthin of formula 3 or of formula 5, wherein a) astaxanthin of the general formula 2 is oxidized in a solvent or in a solvent mixture in the presence of at least one tertiary alcoholate to form astacene of formula 1, preferably according to at least one of the previously described embodiments, b) astacene of formula 1 is reduced by means of an enantioselective transfer hydrogenation to form 3S,3'S-astaxanthin of formula 3,

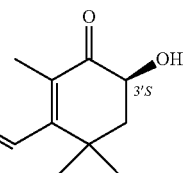
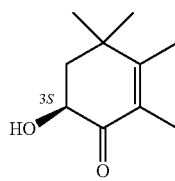

(3)

or 3R,3'R-astaxanthin of formula 5

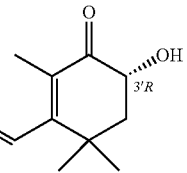
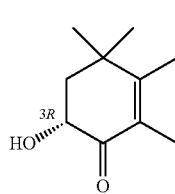

(5)

with the exocyclic double bonds of 3S,3'S-astaxanthin of formula 3 or of 3R,3'R-astaxanthin of formula 5 having either an E- or E- and/or Z configuration.

This process provides a hitherto unknown short and simple route of transforming racemic astaxanthin of formula 2 into 3S,3'S-astaxanthin of formula 3 or 3R,3'R-astaxanthin of formula 5. The whole reaction sequence requires between 8 and 25 h and is pretty fast. It provides an overall yield based on astaxanthin of general formula 2 ranging from 60 to 70%. Due to the straight alignment of steps a) and b) this process is cheap, energy-saving and provides high yields of the required astaxanthin enantiomer 3 or 5, as can be seen from the examples below. The enantiomeric excess of compound 3 or of compound 5 is 100% and the diastereomeric excess is 93%, which is to say, that forming the respective other optical active antipode 3 or 5 is almost completely suppressed.

Let alone the considerable smoothness of this inventive process continuation mentioned supra, it is even more surprising, that in a further embodiment the astacene of formula 1 obtained in process step a), without any workup, is reduced by means of an enantioselective transfer hydrogenation to form 3S,3'S-astaxanthin of formula 3 or 3R,3'R-astaxanthin of formula 5.

One has to bear in mind, that from process step a) tertiary alcoholate and the corresponding alcoholate counter ion—and for some embodiments also the metal salt or the transition metal salt—still remain in the reaction mixture during enantioselective transfer hydrogenation in step b). It is rather astonishing, that these reactants do not interfere with the reactants of the enantioselective transfer hydrogenation of step b), since step a) is an oxidation reaction whereas step b) is a selective reduction reaction. For instance it would be expected from the skilled person that the presence of tertiary butanolate or TMEDA or Mn(II)acetate (cf. examples below) in process step a) would have an impact on the outcome of process step b) and the compounds used therewith, which however, is not observed.

Being able to conduct step a) and step b) "without any work up" in between makes this process pretty fast and cheap as it reduces the amount of purification steps and of by-products formed. Cumbersome treatment or processing of intermediates or crude products is avoided.

The process of converting racemic astaxanthin into enantiomerically pure astaxanthin of formula 3 or of formula 5 or into astaxanthin highly enriched in astaxanthin of formula 3 or of formula 5 in an extended embodiment determines the enantioselective transfer hydrogenation being realized with a combination of formic acid and a transition metal catalyst, said transition metal catalyst comprising at least one ligand, which is selected from the group consisting of at least one optically active amine, which is preferably $H_2N$—CHPh-CHPh-OH, $H_2N$—CHMe-CHPh-OH, MeHNCHMe-CHPh-OH, TsNH—CHPh-CHPh-$NH_2$, (1S,2S)—N-p-toluene sulfonyl-1,2-diphenylethylene diamine, (1R,2R)—N-p-touluene sulfonyl-1,2-diphenylethylene diamine, N-[(1S,2S)-1,2-diphenyl-2-(2-(4-methylbenzyloxy)ethylamino)-ethyl]-4-methylbenzene sulfonamide or N-[(1R,2R)-1,2-diphenyl-2-(2-(4-methylbenzyloxy)ethylamino)-ethyl]-4-methylbenzene sulfonamide; at least one optically active amino acid, and in a highly preferred embodiment the at least one ligand is selected from the group consisting of $H_2N$—CHPh-CHPh-OH, $H_2N$—CHMe-CHPh-OH, MeHN—CHMeCHPh-OH, TsNH—CHPh-CHPh-$NH_2$, (1S,2S)—N-p-toluene sulfonyl-1,2-diphenylethylene diamine, (1R,2R)—N-p-toluene sulfonyl-1,2-diphenylethylendiamine, N-[(1S,2S)-1,2-diphenyl-2-(2-(4-methylbenzyloxy)ethylamino)-ethyl]-4-methylbenzene sulfonamid, N-[(1R,2R)-1,2-diphenyl-2-(2-(4-methylbenzyloxy)ethylamino)-ethyl]-4-methylbenzene sulfonamid.

The transfer hydrogenation was shown to bring particularly high yields of the required compound 3 or 5, when formic acid is used as reduction means. Other reducing agents (e.g. secondary alcohols) instead of or together with formic acid can also be used as reduction means for the enantioselective transfer hydrogentation, however, they provide lower yields and/or lower conversion rates.

Other reduction means are selected from the group consisting of isopropanol, 2-butanol, cyclohexanol.

This is to say, another embodiment of the invention discloses a process for preparing from a mixture of various astaxanthin isomers referred to as astaxanthin of the general formula 2 an enantiomerically pure astaxanthin of formula 3 or of formula 5, or an astaxanthin highly enriched in astaxanthin of formula 3 or of formula 5, wherein a) astaxanthin of the general formula 2 is oxidized in a solvent or in a solvent mixture in the presence of at least one tertiary alcoholate, preferably according to any one of the previously mentioned embodiments, to form astacene of formula 1, b) astacene of formula 1 is reduced by means of an enantioselective transfer hydrogenation to form 3S,3'S-astaxanthin of formula 3,

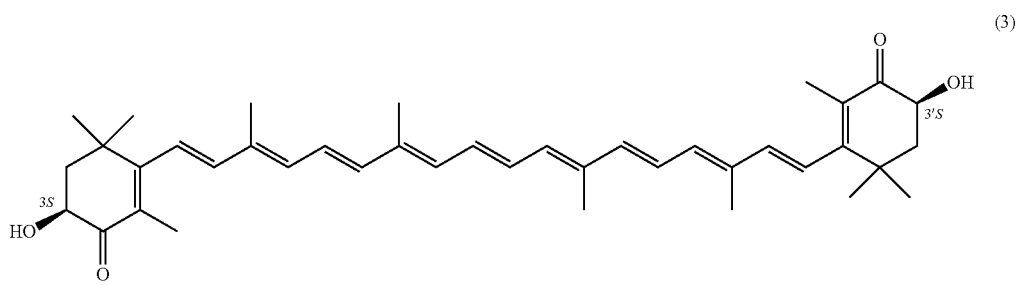 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

(3)

or 3R,3'R-astaxanthin of formula 5

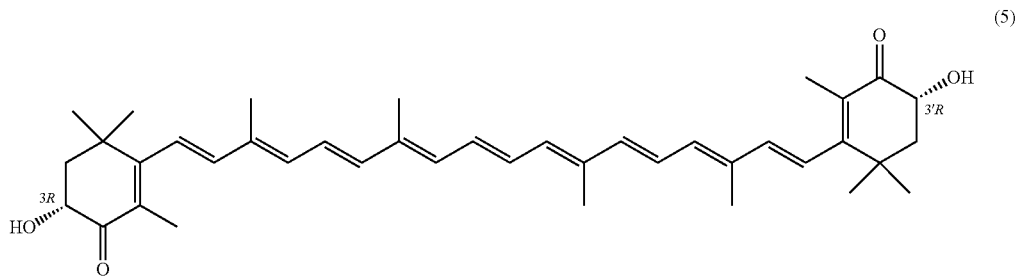

with the exocyclic double bonds of 3S,3'S-astaxanthin of formula 3 or of 3R,3'R-astaxanthin of formula 5 having either an E- or E- and/or Z configuration, the enantioselective transfer hydrogenation being realized with a combination of at least one compound selected from the group consisting of formic acid, isopropanol, 2-butanol, cyclohexanol, and a transition metal catalyst, said transition metal catalyst comprising at least one ligand, which is selected from the group consisting of at least one optically active amine, which is preferably H₂N—CHPh-CHPh-OH, H₂NCHMe-CHPh-OH, MeHN—CHMe-CHPh-OH, TsNH—CHPh-CHPh-NH₂, (1S,2S)—N-p-touluene sulfonyl-1,2-diphenylethylene diamine, (1R,2R)—N-p-toluene sulfonyl-1,2-diphenylethylenediamine, N-[(1S,2S)-1,2-diphenyl-2-(2-(4-methylbenzyloxy)ethylamino)-ethyl]-4-methylbenzene sulfonamide or N-[(1R,2R)-1,2-diphenyl-2-(2-(4-methylbenzyloxy)ethylamino)-ethyl]-4-methylbenzene sulfonamide; at least one optically active amino acid and in a highly preferred embodiment the at least one ligand is selected from the group consisting of H₂N—CHPh-CHPh-OH, H₂N—CHMeCHPh-OH, MeHN—CHMe-CHPh-OH, TsNH—CHPh-CHPh-NH₂, (1S,2S)—N-p-touluene sulfonyl-1,2-diphenylethylene diamine, (1R,2R)—N-p-touluene sulfonyl-1,2-diphenylethylene diamine, N-[(1S,2S)-1,2-diphenyl-2-(2-(4-methylbenzyloxy)ethylamino)-ethyl]-4-methylbenzene sulfonamid, N-[(1R,2R)-1,2-diphenyl-2-(2-(4-methylbenzyloxy)ethylamino)-ethyl]-4-methylbenzene sulfonamid.

More details on the enantioselective transfer hydrogenation can be taken from WO 2016/0237-32 A1 the contents of which is fully incorporated into this disclosure by reference.

It is astonishing, that complex cyclohexadienolones like astacene are able to be selectively reduced in position 3 by a combination of the reduction means and the transition metal catalyst as indicated supra.

The inventive process continuation of converting a mixture of various astaxanthin isomers of general formula 2 into 3S,3'S-astaxanthin of formula 3 or into 3R,3'R-astaxanthin of formula 5 can be even further improved, if one partially or completely exchanges the solvent or solvent mixture used in step a) prior to step b).

This means, running step a), partially or completely exchanging the solvent used and only then running step b) is more efficient in terms of yield, compared to a process without (partial) solvent exchange. By this measure the reaction mixture of step b) is more readily transformed into 3S,3'S-astaxanthin of formula 3 or into 3R,3'R-astaxanthin of formula 5. Furthermore these compounds are much easier crystallized, compared to obtaining/keeping them in the solvent or solvent mixture of step a).

A still further developed embodiment of the continued inventive process discloses preparing from a mixture of various astaxanthin isomers of general formula 2 an enantiomerically pure astaxanthin of formula 3 or of formula 5, or an astaxanthin highly enriched in astaxanthin of formula 3 or of formula 5, wherein a) astaxanthin of the general formula 2 is oxidized in a solvent or in a solvent mixture in the presence of at least one tertiary alcoholate to form astacene of formula 1, b) astacene of formula 1 is reduced by means of an enantioselective transfer hydrogenation to form 3S,3'S-astaxanthin of formula 3,

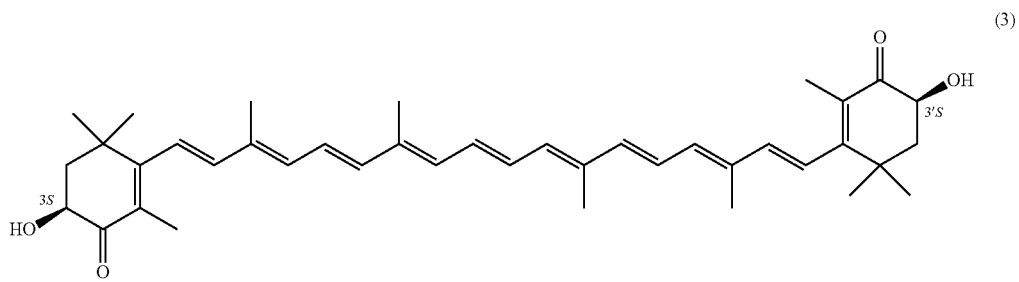

or 3R,3'R-astaxanthin of formula 5

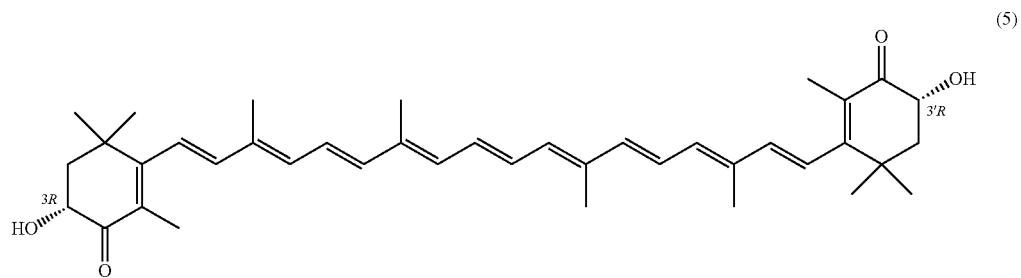 [SMILES: CC1=C(/C=C/C(C)=C/C=C/C(C)=C/C=C/C=C(C)/C=C/C=C(C)/C=C/C2=C(C)C(=O)[C@H](O)CC2(C)C)C(C)(C)C[C@@H](O)C1=O]

(5)

with the exocyclic double bonds of 3S,3'S-astaxanthin of formula 3 or of 3R,3'R-astaxanthin of formula 5 having either an E- or E- and/or Z configuration, and step b) being realized under inert gas.

This is to say, that at the end of step a) one flushes the flask, vessel or reactor with nitrogen or argon, maintains the reaction mixture under inert gas and conducts step b) under inert gas.

This further inventive measure prevents slowing down step b) due to the presence of oxygen traces or entities being able to oxidize or at least alter the reduction means and/or the transition metal catalyst, and/or the at least one ligand of said transition metal catalyst.

Yet another embodiment of the continued inventive process stipulates after process step b) heating up to a temperature of 60 to 120° C., preferably of up to 80 to 110° C. and in a highly preferred embodiment of up to 90 to 106° C. being realized in process step c).

This embodiment is granted importance since it imparts to 3S,3'S-astaxanthin of formula 3 or 3R,3'R-astaxanthin of formula 5 to be very homogeneous in shape. In particular it conveys to the compounds of formula 3 or of formula 5 to uniformly adopt an all-trans or all-E configuration.

The compounds 3S,3'S-astaxanthin of formula 3 or 3R,3'R-astaxanthin of formula 5 are required to be highly pure for many applications. Especially for using them in food supplements or pharmaceuticals, remaining reagents and especially metal traces have to be avoided to the best possible.

This is achieved with a still further continued process for preparing from a mixture of various astaxanthin isomers of general formula 2 an enantiomerically pure astaxanthin of formula 3 or of formula 5, or an astaxanthin highly enriched in astaxanthin of formula 3 or of formula 5, wherein a) astaxanthin of the general formula 2 is oxidized in a solvent or in a solvent mixture in the presence of at least one tertiary alcoholate to form astacene of formula 1; b) astacene of formula 1 is reduced by means of an enantioselective transfer hydrogenation to form 3S,3'S-astaxanthin of formula 3,

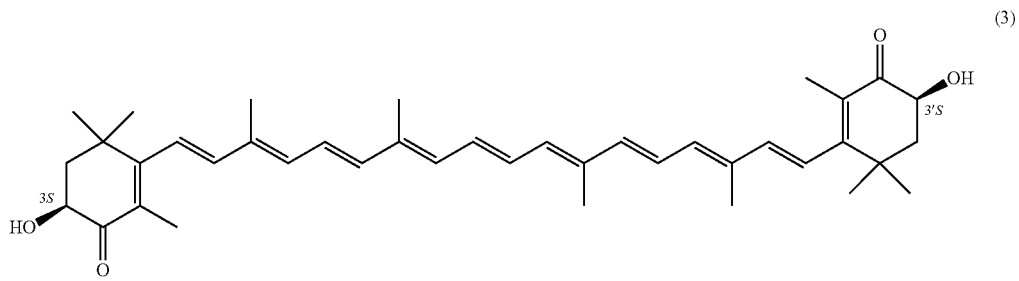

(3)

or 3R,3'R-astaxanthin of formula 5

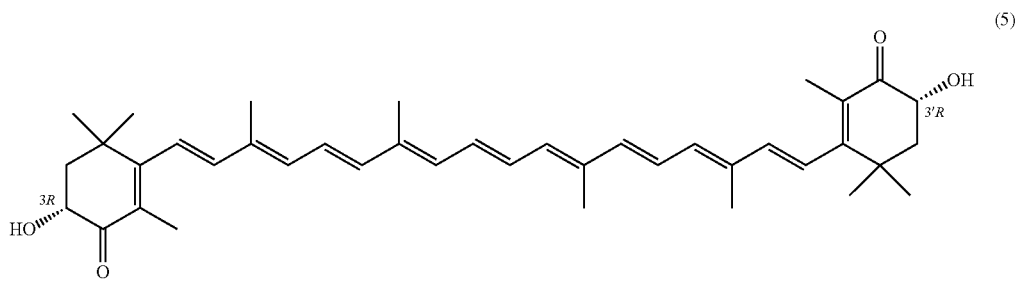 [SMILES: CC1=C(/C=C/C(C)=C/C=C/C(C)=C/C=C/C=C(C)/C=C/C=C(C)/C=C/C2=C(C)C(=O)[C@H](O)CC2(C)C)C(C)(C)C[C@@H](O)C1=O]

(5)

with the exocyclic double bonds of 3S,3'S-astaxanthin of formula 3 or of 3R,3'R-astaxanthin of formula 5 having either an E- or E- and/or Z configuration; after process step b) heating up to a temperature of 60 to 120° C., preferably of up to 80 to 110° C. and in a highly preferred embodiment of up to 90 to 106° C. is realized in process step c) and said heating in process step c) is realized in methanol and/or by repeatedly adding silica to the reaction mixture of process step c).

Silica within this disclosure is understood to mean any type of silicium dioxide (e.g. a granular, vitreous, porous form).

Working in methanol and/or repeatedly adding silica to the reaction mixture of step c) were found to eliminate reagent traces and especially metal traces to a considerable extent. For instance when working with methanol in step c), only 75 ppm of metal were found in 3S,3'S-astaxanthin of formula 3 or of 3R,3'R-astaxanthin of formula 5. Upon using silica 105 ppm of metal were found. Somewhat less good results were obtained by treatment with the strongly acidic resin Amberlyst® 15 or by extraction with aqueous ammonia. Without said treatment the amount of metal traces was 920 ppm in 3S,3'S-astaxanthin of formula 3 or in 3R,3'R-astaxanthin of formula 5.

As mentioned supra, the process for making 3S,3'S-astaxanthin of formula 3 or of 3R,3'R-astaxanthin of formula 5 out of a mixture of various astaxanthin isomers of general formula 2 is required to be cheap and straightforward. This need is supported by the further embodiment of the continued inventive process, wherein the process steps a) and b) and preferably the process steps a), b) and c) are realized "onepot".

By doing so, not only the number of vessels, flasks, receptacles etc. is reduced but also the reaction time is considerably speeded up and the energy spent is reduced at the same time. Likewise one avoids cumbersome treatment or processing of intermediates or crude products.

These advantages hold even more for the following continued embodiment disclosing a process for preparing from a mixture of various astaxanthin isomers referred to as astaxanthin of the general formula 2 an enantiomerically pure astaxanthin of formula 3 or of formula 5, or an astaxanthin highly enriched in astaxanthin of formula 3 or of formula 5, wherein a) astaxanthin of the general formula 2 is oxidized in a solvent or in a solvent mixture in the presence of at least one tertiary alcoholate, the amount of all tertiary alcoholate used ranging from 2 to 20 molar equivalents based on the amount of astaxanthin 2 used, preferably from 2 to 10 molar equivalents, even more preferred from 3 to 8 molar equivalents and mostly preferred from 4 to 6 molar equivalents to form astacene of formula 1, b) astacene of formula 1 is reduced by means of an enantioselective transfer hydrogenation to form 3S,3'S-astaxanthin of formula 3,

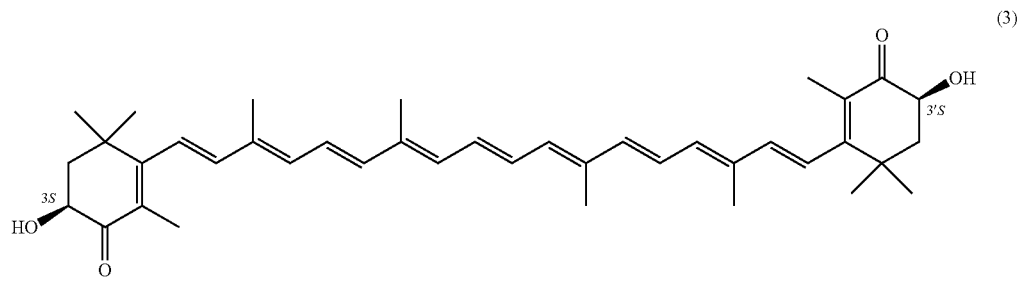 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

(3)

or 3R,3'R-astaxanthin of formula 5

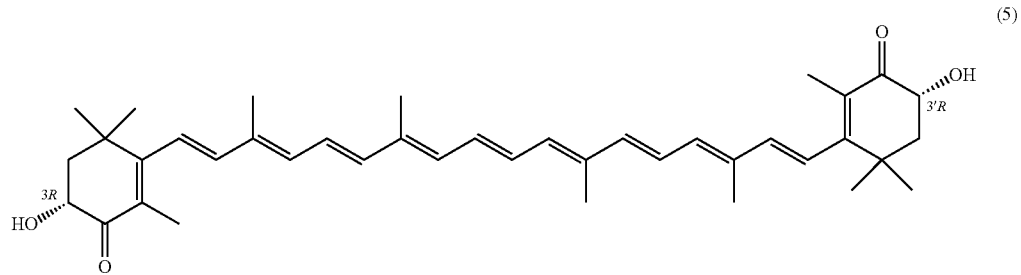 [SMILES: CC1=C(/C=C/C(C)=C/C=C/C(C)=C/C=C/C=C(C)/C=C/C=C(C)/C=C/C2=C(C)C(=O)[C@H](O)CC2(C)C)C(C)(C)C[C@@H](O)C1=O]

(5)

with the exocyclic double bonds of 3S,3'S-astaxanthin of formula 3 or of 3R,3'R-astaxanthin of formula 5 having either an E- or E- and/or Z configuration: and process steps a) and b) and preferably process steps a), b) and c) being realized "onepot".

When inventive experiments were realized using the "onepot" protocol, it was observed that the amount of all tertiary alcoholate employed should be as previously mentioned in order to still obtain high yields of astaxanthin of formula 3 or of formula 5 and this preferably at high reaction rates.

A further embodiment of the invention is a non-therapeutic preparation comprising enantiomerically pure astaxanthin of formula 3 or of formula 5, or an astaxanthin highly enriched in astaxanthin of formula 3 or of formula 5 all obtained with the inventive process. A typical non-therapeutic preparation containing enantiomerically pure or highly enrichted astaxanthin of formula 3 or of formula 5 comprises 14 mg of 3S,3'S-astaxanthin of formula 3, 16 mg of vitamin C, microcrystalline cellulose as capsule filler and hydroxypropylmethylcellulose as capsule shell.

Yet another embodiment of the invention is a preparation for a pharmaceutical or medical use comprising enantiomerically pure astaxanthin of formula 3 or of formula 5, or an astaxanthin highly enriched in astaxanthin of formula 3 or of formula 5 all obtained with the inventive process. A typical preparation for a pharmaceutical or medical use contains 6 mg of enantiomerically pure or highly enriched astaxanthin of formula 3 or of formula 5, 15 IU of vitamin E, 75 w % of oleic acid, 20% of linoleic acid, 5 w % of palmitic acid with the weight amount of all fatty acids giving 100% and making from 60 to 80 w % of the preparation of pharmaceutical or medical use. Said preparation further comprises a standard gel cap comprising gelatin, glycerol and water said gel cap being the container for the aforementioned compounds.

The invention will now be further explained by way of the following examples, which however, in no way are to reduce the inventive idea but are for illustrating purposes only.

Potency [%] and yield in [%] were determined as follows: Samples of the respective product obtained were dissolved in a solvent mixture of acetonitrile/chloroform and injected into a Zorbax Extend C18 column of Agilent the latter being installed in an Agilent Series 1100 HPLC. Elution was realized with a solvent system comprising water as solvent A and acetonitrile/2-propanol (1:1) as solvent B. The w % of the respective compound obtained was determined according to the equation w % equals (peak area×100×response factor)/initial weight of the sample with response factor being defined as initial weight of the sample/peak area. A value of 100 a % means appearance of one peak making an area of 100% viz. 100 a %.

The enantiomeric excess and the diastereomeric excess were determined on a 2× Chirex(R)-PGLY column supplemented with a solvent mixture of dichloromethane n-heptane ethanol containing the sample to be analyzed.

EXAMPLE 1 TO 6

142.5 g (1.92 mol) of tert.-butanol, 28.2 g (251.3 mmol, 20 molar equivalents) of potassium-tert.-butanolate, 29.21 g (0.25 mmol, 0.02 molar equivalents) of N,N,N,N-tetramethylethylendiamine and the metal salt shown in table 1 below were placed at 40° C. in a 1000 ml three-necked flask. The flask's headspace was simultaneously purged with nitrogen (45.3 l/h) and air (22.8 l/h). During a time span of 1 h, 7.5 g (12.57 mmol) of astaxanthin of general formula 2 (isomeric ratio R,R:R,S:S,S=1:2:1) were evenly added in 7 distinct portions under thorough stirring (500 r.p.m.). Stirring was continued for another hour while constantly purging the flask. Thereafter one supplements the reaction mixture with 350 ml of dichloromethane and 18.9 g of acetic acid. Said mixture is then washed with 100 ml of water, with 126 g of saturated sodium bicarbonate solution and again with 100 ml of water. The organic phase is removed under reduced pressure and the remainder analyzed without any further purification.

| Example | Metal Salt [mol %] Nitrogen Compound [mol %] | Weigh-out Quantity [g] | Potency [%] | Yield [%] |
|---|---|---|---|---|
| 1 | Mn-(II)-acetate 1 TMEDA 2 | 7.6 | 79.3 | 81 |
| 2 | Co-(II)-acetate 1 TMEDA 2 | 7.5 | 76.8 | 77 |
| 3 | Fe-(II)-acetate 1 TMEDA2 | 7.2 | 80.5 | 78 |
| 4 | Ru-(III)-chloride 1 TMEDA 3 | 7.9 | 66.8 | 71 |
| 5 | Cu-(II)-acetate 1 TMEDA 2 | 7.7 | 74.7 | 77 |
| 6 | — | 7.9 | 56.6 | 60 |

EXAMPLES 7 TO 9

Influence of Type of Gas Injection, Temperature and Solvent

These examples were realized as previously indicated for example 5, however, in 2-methyl-butan-2-ol. Temperature and type of gas injection were varied.

| Example | Gas Injection Type | Temperature [° C.] | Potency [%] | Yield [%] |
|---|---|---|---|---|
| 7 | headspace purging | 40 | 64.9 | 67.5 |
| 8 | headspace purging | 20 | 67.5 | 70.9 |
| 9 | injection into liquid | 0 | 68.0 | 72.3 |

One observes t-butanol to be superior with respect to yield and compound solubility compared to 2-methyl-butan-2-ol. Temperature was shown to have a yield enhancing effect in 2-methylbutan-2-ol, the lower it is.

EXAMPLES 10 TO 11

Variation of Amount and Composition of Gas, Variation of Amount of Potassium-Tert.-Butanolate Used and Reaction Time Examples 10 to 11 were realized like example 9 at 0° C., however with an amount of only 10 molar equivalents of potassium-tert.-butanolate and in an air atmosphere under variable reaction times.

| Example | Amount Air [l/h] | Reaction Time [h] | Potency [%] | Yield [%] | Byproduct Semiastacene [%] | Overoxidized Products [%] |
|---|---|---|---|---|---|---|
| 10 | 30 | 10.5 | 68.2 | 66.8 | 10 | 3.4 |
| 11 | 90 | 17 | 66.1 | 62.5 | 11 | 8.2 |

One realizes that product formation in an air atmosphere requires a longer reaction time and the amount of byproducts and over-oxidized products increases with reaction time.

EXAMPLE 12

Variation of the Amount of TMEDA and Potassium-Tert.-Butanolate

Example 12 was realized like example 1, however with altering the amount of TMEDA and/or potassium-tert.-butanolate.

| Example | TMEDA Molar Equivalent | KO-tBu Molar Equivalent | Potency [%] | Yield [%] |
|---------|------------------------|-------------------------|-------------|-----------|
| 1       | 0.02                   | 20                      | 79.3        | 81.0      |
| 12      | 0                      | 4                       | 73.5        | 72.8      |

Still satisfying yields of astacene 1 are obtained in short reaction times with omitting the nitrogen compound TMEDA when using reduced amounts of potassium-tert.-butanolate.

EXAMPLE 13

1490 g (20.1 mmol) of tert.-butanol, 75.2 g (0.67 mol, 4 molar equivalents) potassium-t-butanolate and 0,289 g (0.0017 mol, 0.01 molar equivalents) of manganese-(II)-acetate were placed at 40° C. in a 2 l miniplant-reactor and said reactor was purged with a gas stream consisting of nitrogen and an oxygen portion of 7 vol %. 10 portions of astaxanthin (in total 100 g, 0.1675 mol, isomeric ratio R,R:R,S:S,S=1:2:1) were equally metered into the reactor over a time span of 145 min. After further reacting the mixture for another 30 minutes, 902 g of solvent were distilled off, followed by adding 401 g of dichloromethane, 77.1 g of formic acid, another 267 g of dichloromethane, 144.1 g of triethylamine, another 802 g of dichloromethane and 1.066 g (0.00168 mol) of chloro {[(1S,2S)-(+)-2-amino-1,2-diphenylethyl]((4-toluenesulfonyl)amido)(p-cymene)}ruthenium(II) and stirring for 22.5 h at 40° C. After adding 0.52 g (0.00335 mol) of 2-mercaptonicotinic acid, one distills off 1.606 g of solvent at 30 to 45° C. under reduced pressure of 500-650 mbar, adds 500 ml of water and again distills off 510.6 g of solvent at 40 to 53° C. at reduced pressure of 150-180 mbar. The remainder was diluted with 1.737 g of dichloromethane, the phases were separated, the aqueous phase was extracted with 334 g of dichloromethane, the combined organic phases were extracted twice with a mixture consisting of 300 g of water and 47 g of methanol after which 1.358 g of solvent were evaporated at ambient pressure. The mixture was then supplemented with 920 g of methanol and distillation under ambient pressure was continued until achieving a boiling temperature of the mixture of 65° C. The remainder thus obtained was heated for 4 h at 106° C. at inherent pressure and cooled down to 0° C. The suspension thus obtained was filtered and the filter cake was washed twice with 99.4 g of methanol and thereafter dried in a vacuum cabinet dryer at a temperature of 20° C. and a reduced pressure of 30 mbar. 68.88 g of (S,S)-astaxanthin (69% yield based on astaxanthin of general formula 2) were obtained (HPLC: 100 a %, enantiomeric excess ee 100%, diastereomeric excess de 93%

One realizes that the invention describes a process for making astacene of formula 1, the exocyclic double bonds thereof having either an E configuration or an E- and/or Z-configuration, wherein astaxanthin of the general formula 2 having asymmetric centers 3 and 3', each of which respectively having an (S)- or (R)-conformation and the exocyclic double bonds of said astaxanthin 2 having either an E- or E- and/or Z configuration, is oxidized in the presence of at least one tertiary alcoholate.

The invention claimed is:

1. A process for making astacene of formula (1), the exocyclic double bonds thereof having either an E configuration or an E- and/or Z-configuration

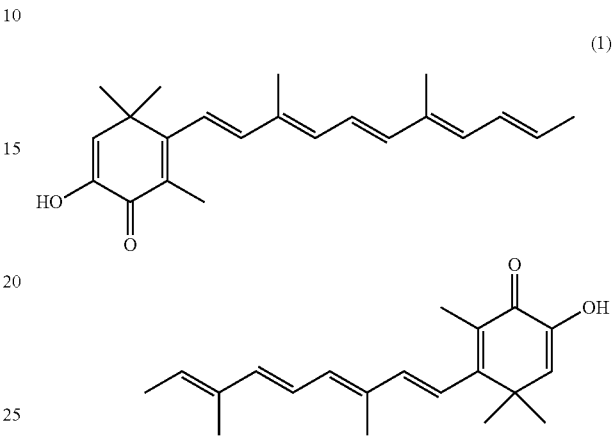

(1)

wherein astaxanthin of the general formula (2)

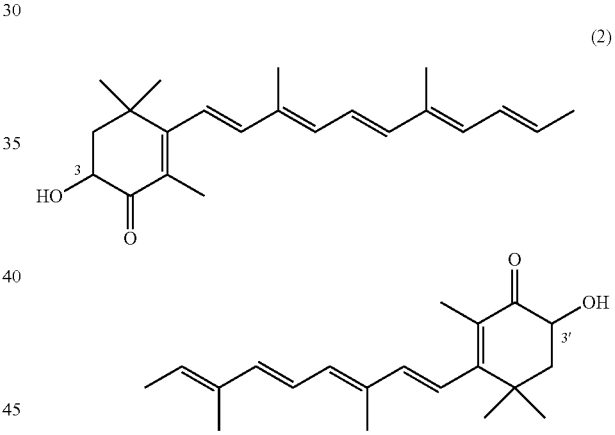

(2)

having asymmetric centers 3 and 3', each of which respectively having an (S)- or (R)-conformation and the exocyclic double bonds of said astaxanthin (2) having either an E- or E- and/or Z configuration, is oxidized in the presence of at least one tertiary alcoholate.

2. The process according to claim 1, wherein the at least one tertiary alcoholate is a tertiary C4-C6 alcoholate.

3. The process according to claim 1, wherein astaxanthin of the general formula (2) is oxidized in the presence of at least one metal salt.

4. The process according to claim 3, wherein the metal salt is a transition metal salt selected from the group of salts of transition metals and/or from the group of oxides of transition metals.

5. The process according to claim 3, wherein the metal salt is a transition metal salt selected from the group of divalent and/or trivalent salts of transition metals of the group consisting of Mn(II), Co(II), Fe(II), Cu(II) and Ru(III).

6. The process according to claim 3, wherein the metal salt comprises at least one anion.

7. The process according to claim 1, wherein the astaxanthin of the general formula (2) is oxidized in the presence of at least one nitrogen compound, said at least one nitrogen compound being selected from the group consisting of, tertiary amines, pyridine, diamines and dipyridine.

8. The process according to claim 1, wherein the astaxanthin of the general formula (2) is oxidized in a time ranging from 0.25 h to 6 h.

9. The process according to claim 1, wherein the astaxanthin of the general formula (2) is oxidized in an atmosphere of an inert gas or in an atmosphere of a mixture of air and an inert gas, or in an air atmosphere, preferably in an atmosphere of an inert gas or in an atmosphere of a mixture of air and an inert gas, said respective atmospheres comprise from 0 to 50 vol % of oxygen.

10. The process according to claim 1, wherein the astaxanthin of the general formula (2) is oxidized in an atmosphere of an inert gas or in an atmosphere of a mixture of air and an inert gas, or in an air atmosphere, preferably in an atmosphere of an inert gas or in an atmosphere of a mixture of air and an inert gas, said respective atmospheres comprise from 7 to 15 vol % of oxygen.

11. A process for preparing from a mixture of various astaxanthin isomers referred to as astaxanthin of the general formula (2)

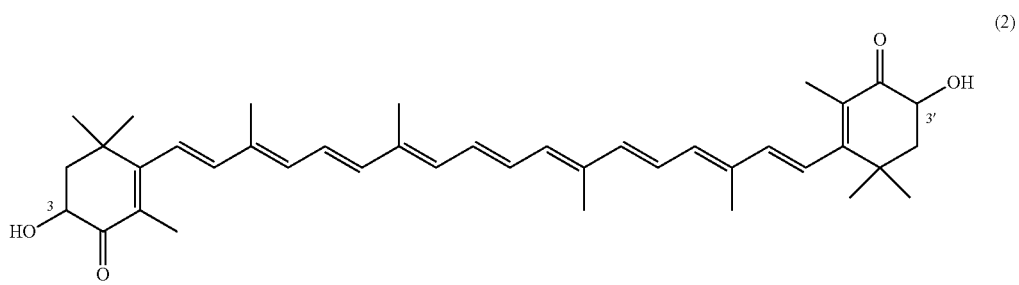

(2)

an enantiomerically pure astaxanthin of formula (3) or of formula (5),
or an astaxanthin highly enriched in astaxanthin of formula (3) or of formula (5), wherein
a) astaxanthin of the general formula (2) is oxidized in a solvent or in a solvent mixture in the presence of at least one tertiary alcoholate according to claim 1, to form astacene of formula (1),
b) astacene of formula (1) is reduced by means of an enantioselective transfer hydrogenation to form 3S,3'S-astaxanthin of formula (3),

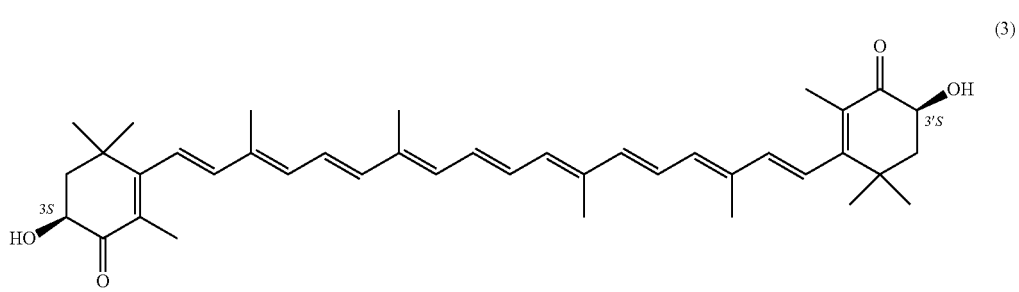 [SMILES: CC1=C(/C=C/C(C)=C/C=C/C(C)=C/C=C/C=C(C)/C=C/C=C(C)/C=C/C2=C(C)C(=O)[C@@H](O)CC2(C)C)C(C)(C)C[C@H](O)C1=O]

(3)

or 3R,3'R-astaxanthin of formula (5)

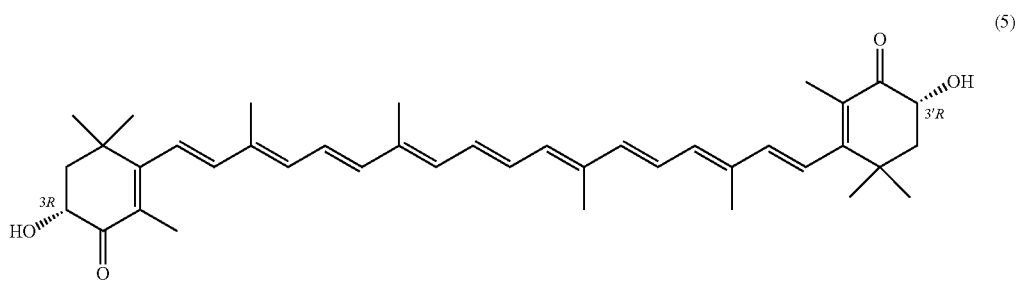

(5)

with the exocyclic double bonds of 3S,3'S-astaxanthin of formula (3) or of 3R,3'R-astaxanthin of formula (5) having either an E- or E- and/or Z configuration.

12. The process according to claim 11, wherein the astacene of formula (1) obtained in process step a), without any workup, is reduced by means of an enantioselective transfer hydrogenation to form 3S,3'S-astaxanthin of formula (3) or 3R,3'R-astaxanthin of formula (5).

13. The process according to claim 11, wherein the enantioselective transfer hydrogenation is realized with a combination of formic acid and a transition metal catalyst, said transition metal catalyst comprises at least one ligand, which is selected from the group consisting of:

at least one optically active amine, which is preferably $H_2N$—CHPh-CHPh-OH, $H_2N$—CHMe-CHPh-OH, MeHN—CHMe-CHPh-OH, TsNH—CHPh-CHPh-$NH_2$, (1S,2S)—N-p-toluene sulfonyl-1,2-diphenylethylene diamine, (1R,2R)—N-p-toluene sulfonyl-1,2-diphenylethylene diamine, N-[(1S,2S)-1,2-diphenyl-2-(2-(4-methylbenzyl-oxy)ethylamino)-ethyl]-4-methylbenzene sulfonamide or N-[(1R,2R)-1,2-diphenyl-2-(2-(4-methylbenzyloxy)ethylamino)-ethyl]-4-methylbenzene sulfonamide;

at least one optically active amino acid.

14. The process according to claim 11, wherein the solvent or solvent mixture used in process step a) is partially or completely exchanged prior to process step b).

15. The process according to claim 11, wherein after process step b) heating up to a temperature of 60 to 120° C., is realized in process step c).

16. The process according to claim 11, wherein the process steps a), b) and c) are realized "onepot".

17. A non-therapeutic preparation comprising enantiomerically pure astaxanthin of formula (3) or of formula (5), or an astaxanthin highly enriched in astaxanthin of formula (3) or of formula (5) all obtained with the process according to claim 11.

18. A preparation for a pharmaceutical or medical use comprising enantiomerically pure astaxanthin of formula (3) or of formula (5), or an astaxanthin highly enriched in astaxanthin of formula (3) or of formula (5) all obtained with the process according to claim 11.

19. The process according to claim 1, wherein the astaxanthin of the general formula (2) is oxidized in an atmosphere of an inert gas or in an atmosphere of a mixture of air and an inert gas, said respective atmospheres comprise from 7 to 15 vol % of oxygen.

20. The preparation claimed in claim 18, wherein the preparation contains 6 mg of enantiomerically pure or highly enriched astaxanthin of formula 3 or of formula 5, 15 IU of vitamin E, 75 w¾ of oleic acid, 20% of linoleic acid, 5 w % of palmitic acid with the weight amount of all fatty acids giving 100% and making from 60 to 80 w¾ of the preparation of pharmaceutical or medical use.

21. The process according to claim 11, wherein the enantioselective transfer hydrogenation is realized with a combination of formic acid and a transition metal catalyst, said transition metal catalyst comprises at least one ligand, which is selected from the group consisting of:

H2N—CHPh-CHPh-OH, H2N—CHMe-CHPh-OH, MeHN—CHMe-CHPh-OH, TsNH—CHPh-CHPh-NH2, (1S,2S)—N-p-toluene sulfonyl-1,2-diphenylethylene diamine, (1R,2R)—N-p-toluene sulfonyl-1,2-diphenylethylene diamine, N-[(1S,2S)-1,2-diphenyl-2-(2-(4-methylbenzyloxy)ethylamino)-ethyl]-4-methylbenzene sulfonamide or N-[(1R,2R)-1,2-diphenyl-2-(2-(4-methylbenzyloxy)ethylamino)-ethyl]-4-methylbenzene sulfonamide; and at least one optically active amino acid.

* * * * *